(12) United States Patent
Lee et al.

(10) Patent No.: US 9,175,025 B2
(45) Date of Patent: Nov. 3, 2015

(54) METHOD FOR PREPARING POROUS ORGANIC-INORGANIC HYBRID MATERIALS

(75) Inventors: U-Hwang Lee, Gyeonggi-do (KR); Jong-San Chang, Dajeon (KR); Young Kyu Hwang, Dajeon (KR); You-Kyong Seo, Busan (KR); Christian Serre, Plaisir (FR); Patricia Horcajada Cortes, Chaville (FR); Hubert Chevreau, Paris (FR); Florence Ragon, Saint Cloud (FR); Thomas Devic, Villebon sur Yvette (FR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 161 days.

(21) Appl. No.: 14/123,161

(22) PCT Filed: Jun. 1, 2012

(86) PCT No.: PCT/KR2012/004363
§ 371 (c)(1),
(2), (4) Date: Mar. 24, 2014

(87) PCT Pub. No.: WO2012/165911
PCT Pub. Date: Dec. 6, 2012

(65) Prior Publication Data
US 2014/0200361 A1    Jul. 17, 2014

(30) Foreign Application Priority Data
Jun. 1, 2011    (KR) .................. 10-2011-0052990

(51) Int. Cl.
| | | |
|---|---|---|
| *C07F 15/02* | (2006.01) | |
| *C07F 7/00* | (2006.01) | |
| *C07F 9/00* | (2006.01) | |
| *B01J 31/16* | (2006.01) | |
| *B01J 35/00* | (2006.01) | |
| *C07F 7/28* | (2006.01) | |
| *B01J 31/22* | (2006.01) | |
| *B01J 20/22* | (2006.01) | |
| *C07C 51/41* | (2006.01) | |
| *B01J 20/28* | (2006.01) | |
| *B01J 20/30* | (2006.01) | |
| *C07C 63/28* | (2006.01) | |
| *C07C 63/333* | (2006.01) | |

(52) U.S. Cl.
CPC .............. *C07F 15/025* (2013.01); *B01J 20/226* (2013.01); *B01J 20/28057* (2013.01); *B01J 20/3085* (2013.01); *B01J 31/1691* (2013.01); *B01J 31/2239* (2013.01); *B01J 35/002* (2013.01); *C07C 51/418* (2013.01); *C07C 63/28* (2013.01); *C07C 63/333* (2013.01); *C07F 7/003* (2013.01); *C07F 7/28* (2013.01); *C07F 9/00* (2013.01); *B01D 2253/204* (2013.01); *B01J 2531/46* (2013.01); *B01J 2531/48* (2013.01); *B01J 2531/56* (2013.01); *B01J 2531/62* (2013.01); *B01J 2531/842* (2013.01); *Y02C 10/08* (2013.01)

(58) Field of Classification Search
CPC .......... C07F 15/025; C07F 7/003; C07F 9/00; B01J 20/3085; B01J 20/226; B01J 20/28057; B01J 31/2239; B01J 31/1691; B01J 35/002; C07C 63/333; C07C 63/28
USPC .............................. 556/42, 51, 146
See application file for complete search history.

(56) References Cited

U.S. PATENT DOCUMENTS

| | | | |
|---|---|---|---|
| 2009/0131703 A1* | 5/2009 | Jhung et al. ................ | 556/44 |
| 2011/0028748 A1* | 2/2011 | Chaplais et al. ............ | 556/1 |
| 2013/0319234 A1* | 12/2013 | Peralta et al. ............... | 95/139 |
| 2015/0158013 A1* | 6/2015 | Eddaoudi et al. ....... | B01J 20/226 |

\* cited by examiner

*Primary Examiner* — Porfirio Nazario Gonzalez
(74) *Attorney, Agent, or Firm* — Ladas & Parry LLP

(57) ABSTRACT

The present invention relates to a method for preparing a porous organic-inorganic hybrid, which comprises gelling a reaction mixture containing a metal precursor, a water-soluble additive and water or water-containing organic solvent at a gelling temperature of 30° C.~100° C. to obtain an organogel-containing solution having a viscosity of 2 to 50,000 (cps), subsequently ageing the solution at said gelling temperature under stirring; and subsequently heating the organogel-containing solution at a temperature between said gelling temperature and 250° C. to crystallize the solution. According to the method for preparation of the present invention, it is possible to commercially practice the present invention since the reaction can be carried out in water or a water-containing organic solvent at an ambient pressure or a slightly raised pressure under a reflux condition, as well as it is possible to mass-produce a porous organic-inorganic hybrid having a high crystallinity and a large surface even in a high mol ratio of 1:1~1:30 of solvent to metal.

20 Claims, 10 Drawing Sheets

2Theta (°)

METHOD FOR PREPARING POROUS ORGANIC-INORGANIC HYBRID MATERIALS

TECHNICAL FIELD

A porous organic-inorganic hybrid can be defined as a porous organic-inorganic polymer compound formed by bonding at least one metal ion with at least one organic ligand, and it is a crystalline compound which includes both organic unit and inorganic unit in the backbone structure and has a porous structure with a molecule-size or nano-size. The porous organic-inorganic hybrid, which is broadly defined, generally refers to as a porous coordination polymer [*Angew. Chem. Int. Ed.*, 43, 2334 (2004)] and also as a metal-organic framework [*Chem. Soc. Rev.*, 32, 276 (2003)]. Recently, researches on porous materials formed by a coordinate bond between at least one metal ion such as Fe, Cr, Al, V, Cu, Ni, Mn and Zn ions and at least one organic ligand such as aromatic carboxylates are actively carried out in various application fields such as catalyst, adsorbent, drug delivery and the like. (Korean Patent Application No. 2006-0011481; Korean Patent Application No. 2007-0049415; Korean Patent Laid-Open No. 2009-0112382; U.S. Pat. No. 6,491,740). Researches on such materials are more actively being carried out recently via combining the molecular coordination bond with the material science.

Since a porous organic-inorganic hybrid has a large surface area and molecular-sized or nano-sized pores, it can be used as adsorbent, gas storage, sensor, membrane, functional thin film, catalyst, catalyst support and the like. Further, it can be used for collecting guest molecules smaller than the pore size or for separating molecules according to their molecular sizes by using the pores.

BACKGROUND ART

A crystalline porous organic-inorganic hybrid is a porous material prepared formed by a coordinate bond between at least one metal ion or metal ion cluster and at least one aromatic carboxylate as an organic ligand. When preparing a porous organic-inorganic hybrid as described above, the solvothermal synthetic method is generally used, but a hydrothermal synthetic method may be used as well in order to increase the hydrothermal stability. As representative porous organic-inorganic hybrids prepared by the above synthetic method, mention can be made of a porous organic-inorganic hybrids having the formula of $Cr_3O(H_2O)_2X[C_6H_3(CO_2)_3]_2$ ($X=F^-$ or $OH^-$) and its hydrate, $Fe_3O(H_2O)_2X[C_6H_3(CO_2)_3]_2$ ($X=F^-$ or $OH^-$) and its hydrate, $Cr_3O(H_2O)_2X[C_6H_4(CO_2)_2]_3$ ($X=F^-$ or $OH^-$) and its hydrate, has been reported [*Science*, 23, 2040 (2005); *Chemical Communications*, 2820 (2007); *Accounts of Chemical Research*, 38, 217 (2005)].

Meanwhile, the coordinate bond between a Group IV metal ion such as Zr or Ti and an organic ligand such as an aromatic carboxylate has a feature that the chemical bonding force is stronger than that of the conventional coordinate bond between a Group III metal ion such as Fe, Cr, Al or the like and a carboxylate ligand. Thus, in recent, active researches on the properties and application of the above materials including Zr or Ti are now carried out [Korean Patent Laid-Open No. 2009-0009849 (corresponding to PCT/EP2007/053704); Korean Patent Laid-Open No. 2009-0033172 (corresponding to PCT/EP2007/053781); WO 2009/133366; WO 2010/0945889; *J. Am. Chem. Soc.*, 130, 13850 (2008); *J. Am. Chem. Soc.*, 131, 10857 (2009)]. In recent, Korean Patent Application No. 10-2009-0089102 (Korean Patent Laid-Open No. 10-2011-0031731) has described a microwave synthesis and solvothermal synthesis of a porous organic-inorganic hybrid containing a tetravalent metal ion using a non-aqueous solvent. Said Korean Patent Application No. 10-2009-0089102 has produced a porous organic-inorganic hybrid comprising tetravalent metal by the solvothermal synthesis method.

CITATION LIST

Patent Literature (Patent literature 1) Korean Patent Laid-Open No. 10-2004-0017726
(Patent literature 2) Japanese Patent Laid-Open No. 1997-002822
(Patent literature 3) U.S. Pat. No. 6,825,260

Non Patent Literature (Non-patent literature 1) Journal of Sol Gel Science and Technology, 13, 305-309 (1998)
(Non-patent literature 2) Microporous and Mesoporous Materials 73, 3-14
(Non-patent literature 3) Chem. Materials 1996, 8, 1667-1681 (1996)

SUMMARY OF INVENTION

Technical Problem in the preparation method according to the above prior art, there are problems that, when the ratio between metal ion and solvent is increased to more than 1:30, the viscosity of the solution is increased and the ununiformity of the solution is deepened to relatively lower the crystallinity of the final product of the porous organic-inorganic hybrid, and accordingly, the porosity such as surface area, pore volume and the like which affect the properties of the nano-pore material is lowered. Therefore, there is much difficulty in mass production of a porous organic-inorganic hybrid having a large surface area and a high crystallinity.

As described in above, although there has been much difficulty in the preparation of a porous organic-inorganic hybrid having a large surface area in a high yield when a reaction mixture contains metal ion and organic ligand in a high concentration, no effective solution has been proposed. The hitherto known methods for preparing a porous organic-inorganic hybrid via gelation show a very low space-time yield (kg/day.m$^3$). Thus, it is keenly necessary to develop a new synthesis method having economic feasibility.

Means for Achieving the Subject

The present inventors have found that, when a reaction mixture comprising a metal precursor, a water-soluble additive and water or a water-containing organic solvent is gelled at a temperature of 30° C.~150° C. which is lower than the crystallization temperature to obtain a organogel-containing solution, and then the organogel-containing solution is aged under stirring and subsequently crystallized at a temperature higher than the above gelling temperature, it is possible to prepare a porous organic-inorganic hybrid having a large surface area and a high crystallinity.

The present inventors have also found that, when the above reaction is carried out under a moderate condition, that is, by using water or a water-containing organic solvent under reflux at a normal pressure or pressurized pressure as well as with a high molar ration of 1:1~1:30 of solvent to metal in the reaction mixture, it is possible to achieve a mass production of the porous organic-inorganic hybrid in a space-time yield of at least 20 kg/day.m³.

Advantage Effect of the Invention

According to the manufacturing method of the present invention, the preparation of the present invention can be commercially practiced since the reaction is carried out in water or a water-containing organic solvent under reflux at a normal pressure or pressurized pressure as well as it is possible to achieve a mass production of the porous organic-inorganic hybrid in a space-time yield of at least 20 kg/day.m³.

EMBODIMENTS FOR CARRYING OUT THE INVENTION

Figure 1:
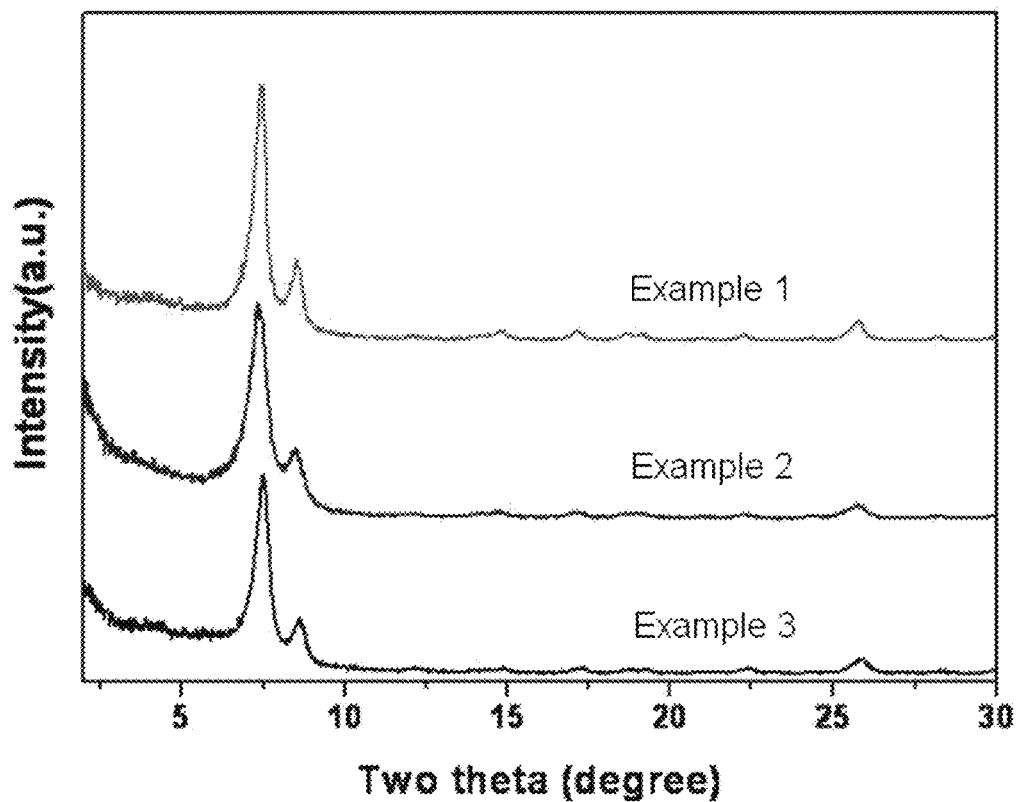
FIG. 1 is an X-ray diffraction pattern of the porous organic-inorganic hybrid (Zr-BDC).

The first propose of the present invention is to provide a method for the preparation of a porous organic-inorganic hybrid material comprising Step 1)~Step 3):

1) a step for obtaining a reaction mixture comprising a metal precursor comprising a metal ion or an oxygen-bonded metal ion cluster, a compound which can act as organic ligand, a water-soluble additive and water or water-containing organic solvent;

2) a step for heating said reaction mixture to a gelling temperature of 30~150° C. to give a organogel-containing solution having a viscosity of 2~50,000 (cps), which is then aged under stirring at the gelling temperature;

3) a step for further heating the resulted organogel-containing solution at a temperature between a temperature higher than said gelling temperature and 250° C. to crystallize the porous organic-inorganic hybrid;

wherein said porous organic-inorganic hybrid material is represented by the following Formula 1:

$$M_aO_bX_cL_d \quad \text{[Formula 1]}$$

(wherein M represents a metal ion or an oxygen-bonded metal ion cluster, O represents an oxygen atom, X represents an anionic ligand, L represents an organic ligand, a represents a rational number of 1 to 12, b represents a rational number of 0 to 6, b represents a rational number of 0 to 18, and d represents a rational number of 1 to 120).

Hereinafter, the present invention is described in more detail.

In the present invention, by means of controlling the nucleation process of the porous organic-inorganic hybrid that contains metal ions and organic ligands to reduce the crystallization time and by means of adding a water-soluble additive such as acid or base to water or a water-containing organic solvent, the crystallinity and surface area of the porous organic-inorganic hybrid can be greatly improved even in a case that the molar ratio of solvent to metal is highly increased to 1:1~30:1, and thereby, it is possible to provide a commercial method for mass production of porous organic-inorganic hybrid having a high crystallinity and surface area in a high space-time yield of at least 20 kg/day/m³, particularly at least 70 kg/day/m³.

In the present invention, the term "gel" means a diluted cross linking system in a jelly form that lies in an intermediate state between a fluid and a perfectly elastic body, and belongs to a colloidal dispersion system but does not flow. The term "organic gel" means a non-crystalline, amorphous and thermoplastic solid material which contains organic compound solution in a three-dimensional cross linking network system. In the present invention, the solution is an organic solvent and the three dimensional cross-linking network system is a coordinate compound of metal ion and organic ligand.

Also, the term "gelling" or "gelation" means a sol-gel change process that starts from the formation of a solid fractal aggregate, goes through a sol state and grows until it expands.

According to the present invention, the gelation is carried out by heating a reaction mixture from room temperature to 150° C., specifically 120° C., particularly 100° C. and then stirring for 0.5~36 hours to have a viscosity of 2 to 50,000 cps to form an organogel-containing solution. The viscosity of the resulted organogel-containing solution is measured by sampling 10 ml of the reaction mixture and using a viscometer. Since the organogel-containing solution forms a 3-dimensional cross-linking network, the employment of the organogel-containing solution in the crystallization step can cause an effect to reduce the crystallization time.

In the present invention, the viscosity of the organogel-containing solution has a range between 3~5000 cps, and preferably 4~2500 cps. When the viscosity is less than 2 cps, there are drawbacks such that the crystallinity is relatively low and the crystallization time is delayed since the crystal nucleation is not sufficient. When the viscosity is more than 50,000 cps, there are drawbacks such that the crystallinity is decreased since agitation is difficult.

In the preparation of the porous organic-inorganic hybrid of the present invention, metal precursor including metal ion or metal ion cluster to which oxygen is bonded can use at least one metal selected from a group consisting of Al, Cr, Hf, Mn, Ti, V, Zr, Ca and Mg.

According to one embodiment of the present invention, the above-mentioned metal may be selected from the group consisting of Al, Cr, Hf, Mn and V. In another preferred embodiment, the above-mentioned metal can be selected from the group consisting of Ti and Zr.

Specifically, said metal ion or metal ion cluster can contain at least one selected from a group consisting of $Ti^{4+}$, $Zr^{4+}$, $Ti^{4+}$, $HF^{4+}$, $Fe^{3+}$, $Fe^{2+}$, $Al^{3+}$, $Cr^{3+}$, $V^{5+}$, $Mn^{3+}$, $Mn^{2+}$, $Ca^{2+}$, $Mg^{2+}$ or the like. Meanwhile, a metal ion cluster to which oxygen is bonded can be selected from a group consisting of $Fe_3O$, $Zr_6O_4$, $Al_{12}O$, $Cr_3O$, $Fe_6O_2$, $Ti_8O_8$, ZrO, or the like.

For example, compounds containing metal ion or metal ion cluster can be selected from a group consisting of metal halide salt, metal oxyhalide salt (e.g. $ZrOCl_2$), metal sulfate salt (e.g. $Ti_2(SO_4)_4$), metal oxysulfate salt (e.g. $TiOSO_4$), metal nitrate salt (e.g. $Fe(NO_3).9H_2O$), metal acetate salt (e.g. iron acetate), metal carbonyl, metal alkoxide and hydrates thereof. Halogen means F, Cl, Br or I.

According to the present invention, the reaction mixture can further comprise a compound (X) which can act as an anionic ligand, and said compound (X) can be selected from a group consisting of inorganic and/or organic compounds containing $OH^-$, $F^-$, $I^-$, $Cl^-$, $Br^-$, $NO_3^-$, $BF_4^-$, $PF_6^-$, $I^-$, $SO_4^{2-}$, $HSO_4^-$ or $R_nCOO^-$ ($R_n$ represents a $C_1$-$C_6$ alkyl group or H).

In the preparation of the porous organic-inorganic hybrid of the present invention, examples of an organic compound (L) which can act as an organic ligand can include an organic compound having at least one coordinatable substituent which can coordinatively bond to metal, and alternatively, mention can be made of an organic compound having at least one potential coordinative substituent which can transform to coordinately bond to metal. The example of coordinative substituent which can coordinately bond to metal can include carbonate group, carboxylic acid group (—$CO_2H$) or its anionic group such as carboxylate group (—$CO_2^-$), amine group (—$NH_2$), nitro group (—$NO_2$), hydroxy group (—OH), halogens group (X), sulfonic acid group ($SO_3H$) or its anionic group ($SO_3^-$), imino group (>C=NH), amide group (—$CONH_2$), methanedithioic acid group (—$CS_2H$) or its anionic group (—$CS^-$), pyridine group and pyrazine group, or the like, but it will not be limited to these group.

Examples of the organic compound having carboxylic acid group or carboxylate group as coordinatable ligand can include benzenedicarboxylic acid, naphthalenedicarboxylic acid, biphenyldicarboxylic acid, azobenzenedicarboxylic acid, azobenzene tetracarboxylic acid, 1,3,5-tris(4-carboxyphenyl)benzene, benzenetricarboxylic acid, benzenetetracarboxylic acid, naphthalenetricarboxylic acid, pyridinedicarboxylic acid, bipyridyldicarboxylic acid, imidazolate, fumaric acid, muconic acid, formic acid, oxalic acid, malonic acid, succinic acid, glutaminic acid, hexanedioic acid, heptandioic acid, cyclohexyldicarboxylic acid, and carboxylate derivatives thereof. Specific examples of the compound having carboxylic acid group or carboxylate group can include 1,4-benzenedicarboxylate, trans-muconic acid, benzenetricarboxylate, 2,6-naphthalenedicarboxylate, phenyl diacetate, phenylene diacrylate, 4,4'-biphenyldicarboxylate, terphenyl dicarboxylate, azobenzenedicarboxylate, and derivatives, solvate and hydrate thereof.

The usable compound having carboxylic acid group or carboxylate group can further contain, in addition to the carboxylic acid group or carboxylate group, at least one other substituent, preferably coodinatable substituent, for example, —$NO_2$, —$NH_2$, —$SO_3H$, Br, Cl, I, —OH, —SH, etc. As examples of compound having other substituent in addition to carboxylic acid group or carboxylate group, mention can be made of 3-amino-1,4-benzenedicarboxylic acid, 3-nitro-1,4-benzenedicarboxylic acid, 3-$HSO_3$-1,4-benzenedicarboxylic acid.

The amount of the organic compound that can act as organic ligand can be suitably adjusted depending on the type of metal component and organic compound to be used. For example, the organic compound which can act as organic ligand can be employed in a ratio of 0.1~500 mol, particularly 0.1~100 mol, preferably 0.1~10 mol based on 1 mol of metal ion, and it is not strictly limited.

In the preparation of the porous organic-inorganic hybrid of the present invention, examples of the water-soluble additive can include acid and base. As water-soluble acid additive, mention can be made of hydrochloric acid (HCl), nitric acid ($HNO_3$), sulfuric acid ($H_2SO_4$), phosphoric acid ($H_3PO_4$), acetic acid, boric acid ($H_3BO_3$) and perchloric acid ($HClO_4$), and as water-soluble salt or base additive, mention can be made of NaCl, $NaHCO_3$, $Na_2CO_3$, NaOH, $NH_4OH$, but is not limited thereto.

The amount of the water-soluble additive can be suitably adjusted depending on the type of metal component and organic compound to be used. For example, water-soluble additive can be employed in a ratio of 0.01~10 mol, specifically 0.05~6 mol, particularly 0.1~3 mol based on 1 mol of metal ion, and it is not strictly limited.

As solvent that can be used in the present invention, mention can be made of solvents that can dissolve metal ions or metal ion-containing compounds as well as organic compounds which can act as organic ligand.

As example of solvent which can be used in the present invention, mention can be made of water, water-containing organic solvents, for example, alcohol, ketone, hydrocarbon, N,N'-dimethylformamide (DMF), diethylformamide (DEF), dimethylacetamide (DMAc), acetonitrile, dioxane, chlorobenzene, pyridine, N-methylpyrrolidone (NMP), sulfolane, tetrahydrofuran (THF), gamma-butyrolactone, C1~C12 alkylamine, but the present invention is not limited thereto. As alcohols, mention can be made of C1~C10 mono- or poly-alcohol, for example, including methanol, ethanol, propanol, alkylene polyol such as ethylene glycol and glycerol, and aliphatic alcohol such as cyclohexanol. As ketones, mention can be made of C2~C10 ketones, for example, including acetone, methyl ethyl ketone, acetylacetone, or the like.

As organic solvent, mention can be preferably made of water-miscible solvent that can be mixed with water and water-soluble solvent that can be dissolved in water.

According to one embodiment of the present invention, a porous organic-inorganic hybrid can be prepared via a crystallization process at a temperature higher than the boiling point of the reaction mixture or solvent and at the natural vapor pressure (Autogenously pressure) by using water and/or a suitable organic solvent containing an acid. As the solvent, dimethylformamide can be advantageously employed since it can dissolve organic acid ligands and remove proton (hydrogen cation) during deprotonation step.

Meanwhile, the present invention can provide a particularly advantageous effect when using a Group IV metal such as Ti or Zr.

In other words, the inventors of the present invention has found that, on the basis that the above metal ions interact strongly with oxygen, when ion cluster wherein metal elements are interconnected with O or OH oxygen species is combined with organic ligand, said metal ions can act as a particularly stable inorganic constituent unit. In addition, the inventor has found that the crystallinity and the porosity feature such as surface area of the porous organic-inorganic hybrid can be improved and extended by comprising a step for gelling a mixture of metal precursor and organic ligand during the preparation of a porous organic-inorganic hybrid, wherein said metal precursor contains the above-mentioned Group IV metal ion or metal ion cluster to which oxygen is bonded.

Further, in case of using a porous organic-inorganic hybrid having the above-mentioned metal atom as an inorganic constitutional unit together with an organic ligand comprising dicarboxylate group, it has been found that the edge of multilateral structure of the porous organic-inorganic hybrid is connected by the carboxylate group of an organic ligand comprising a dicarboxylate group and thus can form a stable structure.

In one embodiment of the present invention. Ti is a Group IV transition metal and has a particularly strong interaction with oxygen, thus, $Ti^{4+}$ ion can be employed as an inorganic constitutional unit of novel porous organic-inorganic hybrids.

In the structure of a porous organic-inorganic hybrid in which the inorganic constitutional unit is Group IV metal ion or compound containing the same, the most labile portion is the inner linkage of organic ligands, not the linkage between organic ligand and inorganic constitutional unit or the structure itself of the porous organic-inorganic hybrid.

In the application of a porous organic-inorganic hybrid, the structural resistance to solvent and the mechanical strength of the porous organic-inorganic hybrid are very important. It is confirmed that a porous organic-inorganic hybrid having the above-mentioned characteristics does not change and is present in a stable state even after stirring for 24 hours in a mixed solvent to which acid or base is added.

In the present invention, as the heating method which can be used in the gelling step and the crystallizing step, mention can be made of ultrasound heating, microwave heating, steam heating, electric heating, hot oil heating, reflux reaction, or the like, but is not limited thereto. In the microwave heating, it is possible to employ a microwave having a frequency of 1~30 GHz, specifically a microwave having the frequency of 2.54 GHz which is commonly used industrially, but is not limited thereto.

In the gelling step, the gelling temperature may be from 30° C. to 100° C., specifically 50° C. or more, 60° C. or more, 80° C. or more or 100° C. or more.

The gelling step is to form an organic-inorganic hybrid network by a coordinate bond of the metal ion with the ligand before reaching a synthetic temperature of a porous organic-inorganic hybrid, and thereby to derives a uniform nucleation along with the balance between the hydrolysis rate of metal ion or metal ion cluster and the dissociation (deprotonation) rate of proton in organic ligands.

At the crystallizing step, the reaction temperature is not restricted and may be 30° C. or more, 60° C. or more, 80° C. or more or 100° C. or more. In general, the crystallizing reaction can be carried out at a temperature which is not less than the above-mentioned gelling temperature, preferably at a temperature which is higher than the above-mentioned gelling temperature. When the solvent is water or a water-containing organic solvent having a high water content, it is possible to carry out the crystallizing reaction at a temperature between the gelling temperature and a temperature 10° C. higher than the gelling temperature.

In an embodiment of the present invention, a porous organic-inorganic hybrid can be prepared via a hydrothermal synthesis by using solvent diffusion around room temperature or by using water as solvent and reacting at a high temperature.

According to one embodiment of the present invention, a porous organic-inorganic hybrid can be prepared via a solvothermal synthesis by using an organic material as solvent [*Microporous Mesoporous Mater.*, Vol. 73, p. 15 (2004)].

At the gelling step and the crystallizing step, the reaction pressure is not substantially restricted. For example, it is possible to carry out the reaction at the autogenous pressure which is automatically established by the reactants at the reaction temperature in the reactor, or at a pressurized pressure established by introducing an inert gas such as nitrogen and helium.

The above-mentioned solvent can be employed in a ratio of 1~30 mol, specifically 2~25 mol, particularly 5~20 mol based on 1 mol of metal ion, but is not limited thereto.

Meanwhile, in case where a porous organic-inorganic hybrid is prepared from a reaction mixture containing a metal precursor, an organic ligand and a solvent and the solvent is employed in a ratio of 30 mol or less to 1 mol of metal ion, when the reaction is continuously proceeded to the crystallization step without ceasing at the gelling step, the uniformity of the reaction solution is decreased due to the high concentration of the metal ion as starting material, and as a result, a porous organic-inorganic hybrid having a very low crystallinity and surface area is obtained.

For those reason, the known methods for preparing a porous organic-inorganic hybrid has carried out the reaction by employing a large amount of solvent compared with metal ion, for example by adding the solvent in tens to hundreds mol ratio to make the concentration of metal ion in the reaction solution very low. Thereby, there has been a restriction in commercial mass production of a porous organic-inorganic hybrid.

The present inventors have found that it is possible to control the hydrolysis rate of metal ions and the dissociation rate of proton of organic ligands by means of adding a water-soluble additive to a reaction mixture containing a metal precursor, a compound that can act as organic ligand and a solvent, and subjecting the resulting reaction mixture to a gelling and optional aging steps at 30° C.~150° C., preferably 30° C.~120° C. before heating the reaction mixture to the crystallizing temperature, and thereby, it is possible to ensure a high crystallinity and high porosity at the crystallization temperature of a porous organic-inorganic hybrid by means of increasing the number of crystal nuclei of the porous organic-inorganic hybrid and uniformly maintaining the distribution of initial gelling particles for crystal growth. In addition, it is possible to increase the crystallinity and surface area of a porous organic-inorganic hybrid by means of controlling the amount of the water-soluble additive including acids, bases or salts to 0.01~10 mol based on 1 mol of metal precursor.

According to one embodiment of the present invention, it is possible to prepare a porous organic-inorganic hybrid having in which water molecules are present between crystals by coordination or hydration by means of gelling and aging a reaction mixture containing a metal precursor, a compound that can act as a organic ligand, a water-soluble additive and water at the atmospheric pressure or a pressurized pressure at a gelling temperature of 80° C.~100° C. and then subsequently crystallizing it.

According to one embodiment of the present invention, it is possible to prepare a porous organic-inorganic hybrid having in which water molecules are coordinated or hydrated between crystals by refluxing a reaction mixture containing a Group IV metal precursor such as Ti or Zr, a compound that can act as a organic ligand, a water-soluble additive and water as solvent at the atmospheric pressure or a pressurized pressure at a gelling temperature of 80° C.~120° C. to carry out the gelling and aging steps, and then even by carrying out the crystallization step at the same conditions or at a temperature which is 10° C.~20° C. higher than the gelling temperature.

In the preparation of a porous organic-inorganic hybrid of the present invention, the porous organic-inorganic hybrid of the following Formula 2 can be particularly mentioned:

$$MO[[(CO_2)_2-C_6H_{4-y}-(X)_y](H_2O)_m].n(H_2O)$$ [Formula 2]

(wherein M represents Ti or Zr, O represents oxygen atom linked to a metal ion cluster, X represents a hydrophilic functional group which is substituted on the benzene ring and selected from —NH$_2$, —NO$_2$, —CO$_2$H or SO$_3$H, y represent an integer of 1 to 4, m represents a rational number of 1 to 20, and n represents a rational number of 0 to 20).

The porous organic-inorganic hybrid material of the above Formula 2 comprises one or more metal ion cluster in which at least one IV metal ion is bonded with and one or more organic ligand having carboxylate functional group(s) that coordinately bond(s) to the metal ion cluster, wherein said organic ligand further contains, in addition to the carboxylate functional group(s), one or more basic, acidic or polar hydrophilic functional group as substituent. The porous organic-inorganic hybrid material of the above Formula 2 is a material wherein the crystals are synthesized and formed in aqueous solution and water molecules in the crystals form hydrogen bonds with said hydrophilic functional group.

As specific examples of the porous organic-inorganic hybrid material of the above Formula 2, mention can be made of the compounds that are novel materials and can be represented by the following Formulae 2a, 2b, 2c, 2d and 2e, wherein it contains at least one carboxylate functional group that coordinately bonded to metal ion cluster as well as at least one basic, acidic or polar hydrophilic functional group selected from —NH$_2$, —NO$_2$, —CO$_2$H or —SO$_3$H and water molecules in the crystals form hydrogen bonds with said hydrophilic functional group:

$$MO[[(CO_2)_2-C_6H_3-NH_2](H_2O)_m].n(H_2O)$$ (Formula 2a), $$MO[[(CO_2)_2-C_6H_3-NO_2](H_2O)_m].n(H_2O)$$ (Formula 2b), $$MO[[(CO_2)_2-C_6H_3-CO_2H]](H_2O)_m].n(H_2O)$$ (Formula 2c), $$MO[[(CO_2)_2-C_6H_2-(CO_2H)_2](H_2O)_m].n(H_2O)$$ (Formula 2d), and $$MO[[(CO_2)_2-C_6H_3-SO_3H]](H_2O)_m].n(H_2O)$$ (Formula 2e)

(wherein M represents Ti or Zr, m represents a rational number of 1 to 20, n represents a rational number of 0 to 20)

The porous organic-inorganic hybrids represented by the Formula 2, which can be advantageously prepared in an aqueous solution, has a feature that they possess extra hydrophilic functional group(s) in addition to 1,4-dicarboxylate ((—CO$_2^-$)$_2$) substituted on benzene ring of the organic ligand and these extra hydrophilic functional group has a acidic, basic and polar functionality to form hydrogen bond with water molecules. Since these materials contain water molecules in its pores of which water molecules have been generally known as well as water molecules which are present between crystals and form a relatively strong hydrogen bond with the hydrophilic functional group, it has been confirmed that they have an improved adsorption speed and adsorption amount at a dried state when compared with porous zirconium dicarboxylate UiO-66(Zr) that are prepared in an organic solvent.

In addition, in the preparation of a porous organic-inorganic hybrid of the present invention, mention can be made of the porous organic-inorganic hybrid materials that are novel materials and can be represented by the following Formula 3a or 3b, wherein said hybrid contains one or more metal ion cluster in which at least one Group IV metal ion and oxygen are bonded and one or more organic ligand having carboxylate functional group(s) that coordinately bond(s) to the metal ion cluster, and said organic ligand is selected from biphenyl-4,4'-dicarboxylic acid (4,4'-BPDC) or 3,3-dichloro-4,4'-azobenzenedicarboxylic acid (4,4'-AzoBDC)), and wherein said porous organic-inorganic hybrid material has a space group of 12/a:

$$MO[(CO_2)_2-(C_{12}H_8)].n(solvent),$$ [Formula 3a]

[Formula 3b]

$$MO[(CO_2)_2-(C_{12}H_6Cl_2N_2)].n(solvent)$$ (Formula 3b)

(wherein M represents Ti or Zr, and n represents a rational number of 0 to 20).

In the above Formulae 3a and 3b, n(solvent) means that n (number) molecules of solvent are coordinately bonded, attached or contained.

The porous organic-inorganic hybrid prepared according to the present invention can be employed as absorbent materials for the storage, separation and the chemical reaction of gas, liquid and solid materials. Examples of gas to be adsorbed can include hydrogen, oxygen, nitrogen, hydrocarbons such as methane, paraffin, olefins, etc., carbon monoxide, hydrogen sulfide, ammonia, formaldehyde, amines, etc., examples of liquid to be adsorbed can include an odor substance such as VOC (volatile organic compounds) and fungicides, etc., and gasoline, diesel, oils, alcohols, etc. Examples of solid to be adsorbed can include a noble metal ion such as Pt, Pd, etc., nanoparticles of less than 5 nm and other harmful substances such as Hg, Cr, etc. Especially, it can be employed for the adsorption/separation of hydrogen and carbon dioxide and as a useful adsorbent of olefin/paraffin, etc. In addition, it can be used in the separation of CO/CO$_2$, the separation of H$_2$S/CO$_2$/CH$_4$, the separation of N$_2$/propane/propylene, and the separation of xylene isomers, the separation of N$_2$/S, the adsorption of organic nitrogen compounds, the adsorption of organic sulfur compounds and the like.

In addition, the porous organic-inorganic hybrid prepared according to the present invention can be used as a heterogeneous catalyst, a acid/base catalyst, a oxidation/reduction catalyst, a photocatalyst, a catalyst carrier, an adsorbent for a heat pump, an adsorbent for a cooler and a water adsorbent.

Hereinafter, the present invention will be explained in more detail with reference to the examples, but the present invention is not limited to the examples.

EXAMPLES

Example 1

Production of a Zirconium Porous Organic-Inorganic Hybrid

In a 50 L plastic container, 14 mol of ZrOCl$_2$.8H$_2$O, 14 mol of terephthalic acid (H$_2$BDC) and 11.84 kg of N,N-dimethylformamide (DMF) solvent were introduced, and then 780 g of aqueous HCl solution (37%) and 2.01 kg of water were additionally added. The resulting reaction mixture was mixed at room temperature under stirring at 50 rpm for 20 minutes.

The resulting reaction mixture is transferred to a 50 L glass reactor equipped with a reflux device, and the temperature was raised from room temperature to 90° C. in a rate of about 5° C./min to form an organic gel. When the viscosity of the resulting gel solution reaches 300 cps, the temperature was maintained for 3 hours with a reduced stirring speed. Thereafter, the resulting reaction mixture was again heated to 120° C., maintained for 12 hours to perform a crystallization reaction, and then cooled to room temperature with a cooling rate of 1° C./min or below.

After the above synthesis, the resulting slurry solution containing the porous organic-inorganic hybrid was filtered with a pressurized filter at room temperature, and washed with N,N-dimethylformamide. To a reactor of SUS 316 material introduced were N,N-dimethylformamide solvent and the filtered porous organic-inorganic hybrid powder, wherein the N,N-dimethylformamide being used in a ratio of 10 mol when compared with powder. The resulting mixture is stirred for 3 hours at 70° C. to dissolve unreacted organic acid ligands and ions which are contained in the powder, and then filtered with a pressure filter. Methanol is again added to the filtered powder, and the resulting mixture is stirred for 3 hours at 60° C. to wash off unreacted metal precursors and ions, and then dried for 12 hours at 70~100° C. in a dry oven to obtain a zirconium-type porous organic-inorganic hybrid (hereinafter, referred to as "Zr-BDC).

The X-ray diffraction pattern of thus obtained zirconium-type porous organic-inorganic hybrid material is illustrated in FIG. 1, which is confirmed to be consistent with the X-ray diffraction pattern of the zirconium-type organic-inorganic hybrid UiO-66(Zr) reported in the reference [*J. Am. Chem. Soc.*, 130, 13850 (2008)]. It is also confirmed that the surface area of the material obtained in the present invention, when measured by the physical adsorption of nitrogen at a temperature of 77 K, is 1550 $m^2/g$ which is 30% higher than the Langmuir surface area of the UiO-66(Zr) of 1187 $m^2/g$ reported in the reference material. In addition, it is also confirmed that the pore volume is also increased by at least 30%. It shows that the synthetic method of the present invention can greatly improve the physical chemical properties including porosity of the materials. Also, the reaction time can be greatly reduced from 24 hours to 12 hours. In particular, the space time yield of the present example, which should be necessarily considered for commercialization, reaches 121 kg/day.$m^3$, which gives a very effective result because it is at least 23 times greater than 5.2 kg/day.$m^3$ reported in the reference document (Korean Patent Laid-Open No. 2009-0033172; the method described in the comparative example 1 in below).

Example 2

Production of a Zirconium Porous Organic-Inorganic Hybrid

In a 1 L-Teflon reactor, 150 mmol of $ZrOCl_2.8H_2O$, 150 mmol of terephthalic acid ($H_2BDC$) and 232 g of N,N-dimethylformamide (DMF) solvent are introduced, and then 9.5 g of 37% HCl aqueous solution and 22 g of water are additionally added, which are stirred for 20 minutes at 50 rpm at room temperature to give a reaction mixture.

The resulting reaction mixture is transferred to a 1000 ml-glass reactor equipped with a reflux device, and the temperature was raised up to 90° C. for gelation. When the viscosity of the resulting gel solution reaches 50 cps, the temperature was maintained for 3 hours. The resulting reaction mixture was again heated to 128° C., maintained for 12 hours to perform a crystallization reaction, then cooled to room temperature and subjected to the purification and drying steps as described in Example 1 to give porous organic-inorganic hybrid powder.

The X-ray diffraction pattern of thus obtained zirconium-type porous organic-inorganic hybrid material is illustrated in FIG. 1, which is confirmed to be consistent with the X-ray diffraction pattern of the zirconium-type organic-inorganic hybrid UiO-66(Zr) reported in the reference. It is also confirmed that the surface area of the material obtained in the present invention, measured by the physical adsorption of nitrogen at a temperature of 77 K, is 1444 $m^2/g$ which is 21% higher than the Langmuir surface area of the UiO-66(Zr) of 1187 $m^2/g$ reported in the reference (see Table 1 in below). Also, the reaction time can be greatly reduced from 24 hours to 12 hours. In particular, the space time yield of this Example, which should be necessarily considered for commercialization, reaches 67 kg/$m^3$.day, which gives a very effective result because it is at least 10 times greater than 5.2 kg/$m^3$.day in the reference document (Korean Patent Laid-Open No. 2009-0033172; the method described in the Comparative Example 1 in below).

Example 3

Preparation of Zirconium-Type Porous Organic-Inorganic Hybrid Containing Amine Group In a 1 L-Teflon reactor, 50 mmol of $ZrOCl_2.8H_2O$, 50 mmol of 2-aminoterephthalic acid ($NH_2$—$H_2BDC$) and 236 g of N,N-dimethylformamide (DMF) solvent are introduced, and then 3.6 g of 37% HCl aqueous solution and 7.2 g of water are additionally added. The resulting reaction mixture is transferred to a 1000 ml-glass reactor equipped with a reflux device, and the temperature was raised up to 90° C. for gelation. When the viscosity of the resulting gel solution reaches 1000 cps, the temperature was maintained for 3 hours. The resulting reaction mixture was again heated to 140° C., maintained for 12 hours to perform a crystallization reaction, then cooled to room temperature and subjected to the purification and drying steps as described in Example 1 to give porous organic-inorganic hybrid powder. The X-ray diffraction pattern of thus obtained zirconium-type porous organic-inorganic hybrid material is confirmed to be consistent with the X-ray diffraction pattern of the zirconium-type organic-inorganic hybrid UiO-66(Zr)_$NH_2$ reported in the reference document [*Chem. Commun.*, 46, 7700 (2010)]. The space time yield of this Example is 120 kg/$m^3$.day. The surface area of the porous organic-inorganic hybrid materials obtained in this Example is 1394 $m^2/g$, measured by the physical adsorption of nitrogen at a temperature of 77 K.

Comparative Example 1

Preparation of a Zirconium-Type Porous Organic-Inorganic Hybrid

In a 1 L-Teflon reactor, $ZrCl_4$, terephthalic acid ($H_2BDC$) and N,N-dimethylfoimamide (DMF) solvent are introduced and stirred at room temperature and at 50 rpm for 20 minutes to give a resulting reaction mixture having a mol ratio of Zr:$H_2BDC$:DMF=1:1:1497. The resulting reaction mixture is irradiated to a microwave (2.54 GHz) on a microwave reactor (Milestone Company) to raise the temperature to 120° C., which is maintained for 2 hours to carry out the crystallization reaction. Thereafter, the purification and drying steps are performed as described in Example 1 to give porous organic-inorganic hybrid (Zr-BDC) powder. The X-ray diffraction pattern of the porous organic-inorganic hybrid obtained this Comparative Example is consistent with the X-ray diffraction pattern of the materials obtained in Example 1 and the final space time yield of this Comparative Example is 5.2 kg/$m^3$.day.

Comparative Example 2

Preparation of Titanium-Type Porous Organic-Inorganic Hybrid

In a 1 L-Teflon reactor, 2.27 mmol of $TiCl_4$, 2.27 mmol of terephthalic acid ($H_2BDC$) and 680 mmol of N,N-dimethylformamide (DMF) are introduced and stirred at room temperature and at 50 rpm for 20 minutes to give a resulting reaction mixture. The resulting reaction mixture is irradiated to a microwave (2.54 GHz) on a microwave reactor (Milestone Company) to raise the temperature to 120° C., which is maintained for 2 hours to carry out the crystallization reaction. Thereafter, the purification and drying steps are performed as described in Example 1 to give titanium-containing porous organic-inorganic hybrid (Ti-BDC) powder. The X-ray diffraction pattern of the porous organic-inorganic hybrid obtained this Comparative Example is similar to the X-ray diffraction pattern of the materials obtained in Example 1 and the final space time yield of this Comparative Example is 6.0 kg/m$^3$.day.

Comparative Example 3

Preparation of Zirconium-Type Porous Organic-Inorganic Hybrid

Powder of porous organic-inorganic hybrid (Zr-BDC) is obtained with the same method described in Example 1 except for the gelation step of Example 1. The X-ray diffraction pattern of the porous organic-inorganic hybrid obtained in this Comparative Example 3 is consistent to that of the material obtained in Example 1, and the final space time yield is 110 kg/m$^3$.day. However, due to the low crystallinity, the Langmuir surface area is 1200 m$^2$/g, which is 29% lower than that of Zr-BDC which is obtained according the a method including gelation step.

TABLE 1

| | Synthesis time (hour) | Yield (%) | Space time yield (kg/m$^3$ · day) | Surface area $S_{Langmuir}$ (m$^2$/g) |
|---|---|---|---|---|
| Example 1 | 12 | 87 | 121 | 1550 |
| Example 2 | 12 | 88 | 67 | 1444 |
| Example 3 | 12 | 88 | 120 | 1394 |
| Comparative Example 1 | 24 | — | 5.2 | 1187 |
| Comparative Example 2 | 24 | — | 6.0 | 635 |
| Comparative Example 3 | 12 | 84 | 110 | 1200 |

Example 4

Figure 2:
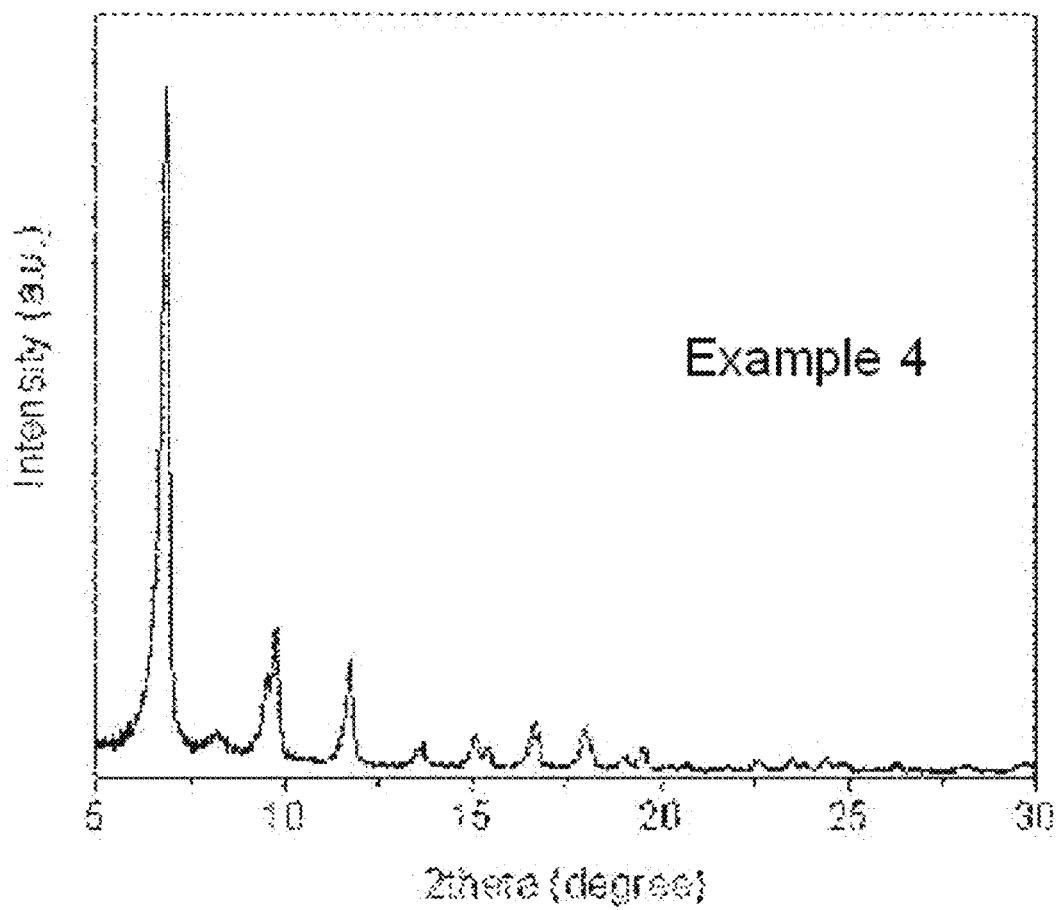
FIG. 2 is an X-ray diffraction pattern of the porous organic-inorganic hybrid (Ti-BDC).

Preparation of Titanium-Type Porous Organic-Inorganic Hybrid Using Metal Alkoxide In a 200 ml-Teflon reactor, 40 mmol of titanium isopropoxide and 60 mmol of terephthalic acid (H$_2$BDC) are introduced, and then 38 g of N,N-dimethylformamide (DMF) solvent and 8 g of methanol are additionally added, which are stirred at room temperature and at 50 rpm for 20 minutes. The resulting reaction mixture is transferred to a 100 ml-glass reactor, and the temperature was raised up to 90° C. to form an organic gel. When the viscosity of the resulting gel solution reaches 20 cps, the stirring speed is lowered and the temperature is maintained for 3 hours. The resulting reaction mixture was introduced into a 150 ml-reflux reactor, maintained at 150° C. for 12 hours to perform the crystallization reaction, and then subjected to the cooling, washing and drying steps as described in Example 1 to give porous organic-inorganic hybrid (Ti-BDC) powder. The crystalline structure of titanium-containing organic-inorganic hybrid is as illustrated in FIG. 2, and it can be confirmed that, although the relative peak intensity is different, the X-ray diffraction pattern has the same diffraction pattern at the same positions with that of porous organic-inorganic hybrid MIL-125(Ti) reported in a reference document [*J. Am. Chem. Soc.*, 131, 10857 (2009)]. The organic-inorganic hybrid obtained in this Example has a surface area of 1380 m$^2$/g, measured by the physical adsorption of nitrogen at a temperature of 77 K, and is and a space time yield of 73 kg/m$^3$.day.

Example 5

Figure 3:
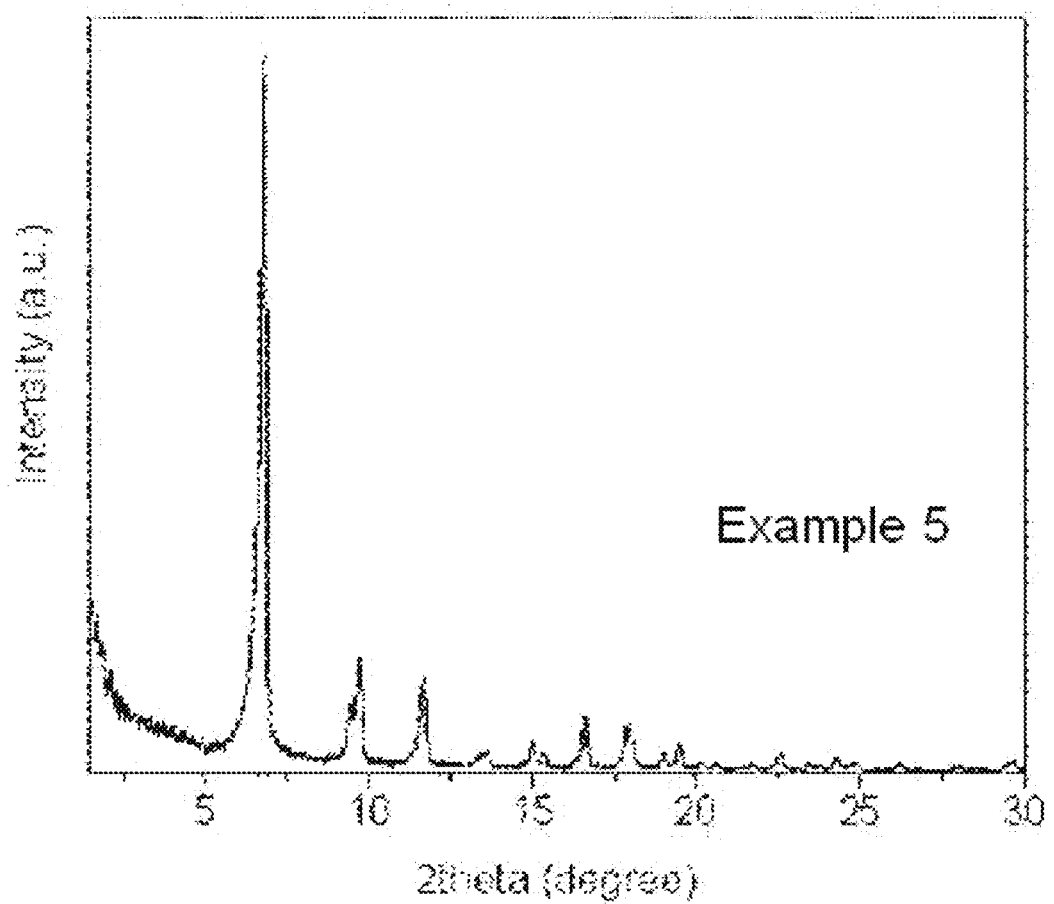
FIG. 3 is an X-ray diffraction pattern of the porous organic-inorganic hybrid ($NH_2$—Ti-BDC).
Figure 4:
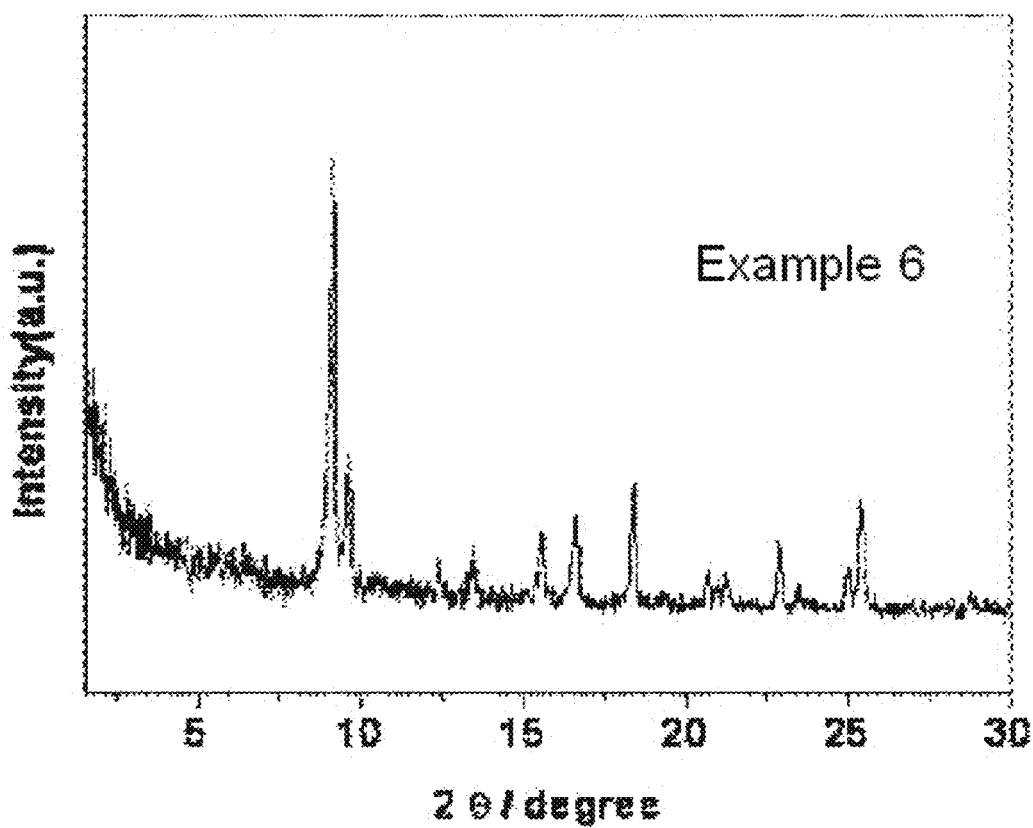
FIG. 4 is an X-ray diffraction pattern of the porous organic-inorganic hybrid (Fe-BDC).

Preparation of an Amine Group-Containing Titanium-Series Porous Organic-Inorganic Hybrid Using Metal Alkoxide In a Teflon reactor, 40 mmol of titanium isopropoxide and 60 mmol of aminoterephthalic acid (NH$_2$-BDC) are introduced, and then 38 g of N,N-dimethylformamide (DMF) solvent and 8 g of methanol are additionally added, which are stirred at room temperature and at 50 rpm for 20 minutes. The resulting reaction mixture is transferred to a 100 ml-glass reactor, and the temperature was raised up to 90° C. to form an organic gel. When the viscosity of the resulting gel solution reaches 50 cps, the temperature is maintained for 3 hours. The resulting reaction mixture was introduced into a Teflon-coated SUS reactor, maintained at 150° C. in a convection oven for 6 hours, 12 hours and 24 hours, respectively, to perform the crystallization reaction, and then subjected to the cooling, washing (with distilled water) and drying steps as described in Example 1 to give porous organic-inorganic hybrid (NH$_2$—Ti-BDC) powder. The X-ray diffraction pattern of thus obtained zirconium-type porous organic-inorganic hybrid material is illustrated in FIG. 3, and it can be confirmed that, although the relative intensity of the peaks are different, the X-ray diffraction pattern has the same diffraction pattern at the same positions with that of porous organic-inorganic hybrid MIL-125(Ti) reported in a reference document [*J. Am. Chem. Soc.*, 131, 10857 (2009)]. The organic-inorganic hybrid obtained in this Example has a surface area of 1350 m$^2$/g, measured by the physical adsorption of nitrogen at a temperature of 77 K, and is and a space time yield of 70 kg/m$^3$.day.

Example 6

Preparation of Iron-Series Porous Organic-Inorganic Hybrid

In a 100 ml three-neck round-bottomed glass flask equipped with a glass condenser, 23.31 g of N,N-dimethylformamide and 9.38 g of 5M aqueous hydrochloric acid are introduced. 25.2 g of Ferrous chloride (FeCl$_3$—H$_2$O) is added and dissolved with stirring and then 15.5 g of Terephthalic acid (H$_2$BDC) is added and stirred for 30 minutes to give a reaction mixture having a molar ratio of Fe:H$_2$BDC:HCl:DMF=1:1:0.4:3.4. The resulting reaction mixture is homogenized by stirred further for 1 hours at room temperature and heated to 70~80° C. for gelation. When the viscosity of the resulting organogel solution reaches 1000 cps, the stirring speed is lowered and maintained for 3 hours. Finally, the resulting reaction mixture is again raised to a reaction temperature of 120° C. and refluxed for 12 hours to carry out the crystallization reaction. After completion of the reaction, the slurry solution containing the products is cooled to room temperature in a cooling rate of 5 □/min and filtered with a pressurized filter to obtain crystals. Thus obtained crystals are added to 300 ml of DMF and stirred at 70° C. for 12 hours, and again filtered with a pressurized filter to remove unreacted terephthalic acid. The X-ray diffraction pattern of thus obtained porous organic-inorganic hybrid is illustrated in FIG. 3, and it can be confirmed that X-ray diffraction pattern has the same diffraction pattern at the same positions with that of porous organic-inorganic hybrid MIL-53(Fe) reported in a reference document [*Chem. Commun.*, 4732 (2008)] and the materials are the same. The organic-inorganic hybrid obtained in this Example has a very high space time yield of 140 kg/m$^3$.day.

Example 7

Preparation of a Nitro Group-Containing Iron-Type Porous Organic-Inorganic Hybrid Example 6 is repeated with exception for using 3-nitro ($NO_2$)-terephthalic acid ($NO_2$—$H_2BDC$) instead of terephthalic acid ($H_2BDC$) to obtain iron-series porous organic-inorganic hybrid. Thus obtained organic-inorganic hybrid has a space time yield of 120 kg/m$^3$.day.

Example 8

Preparation of Iron-Type Porous Organic-Inorganic Hybrid

Figure 5:
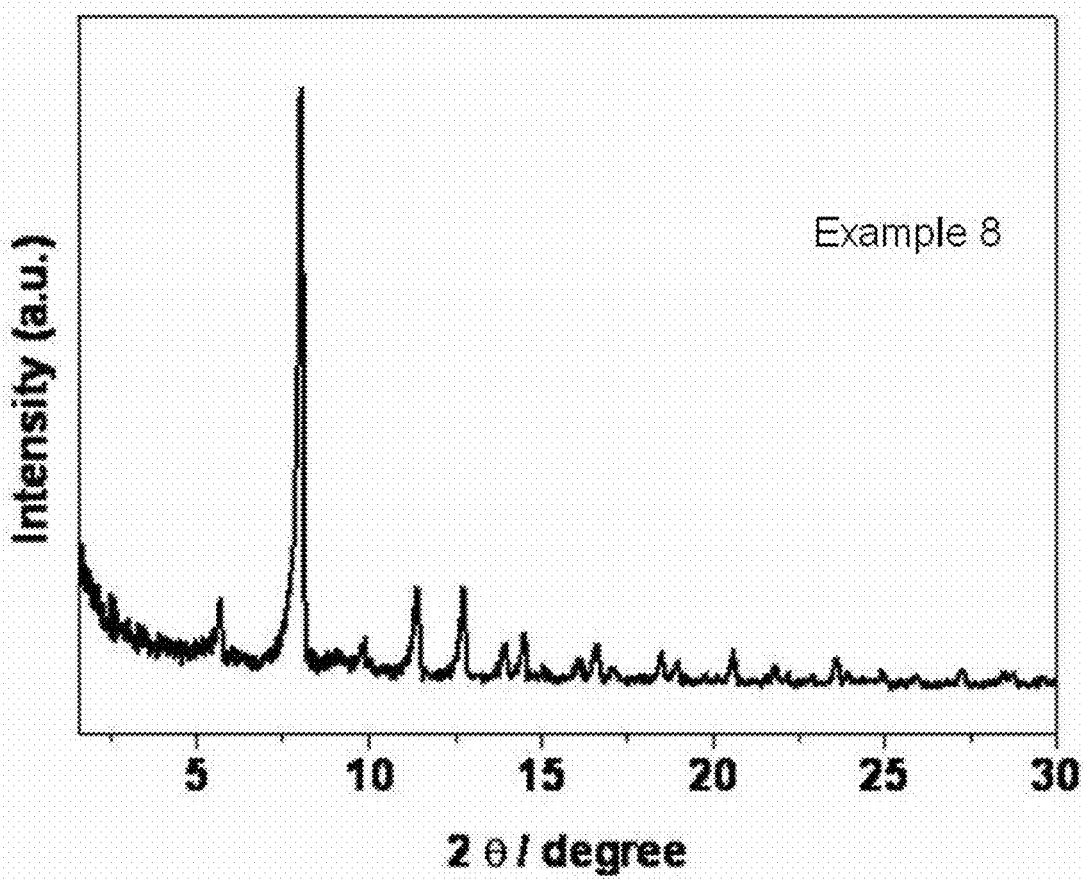
FIG. 5 is an X-ray diffraction pattern of the porous organic-inorganic hybrid (Fe-AzoBTC).
Figure 6:
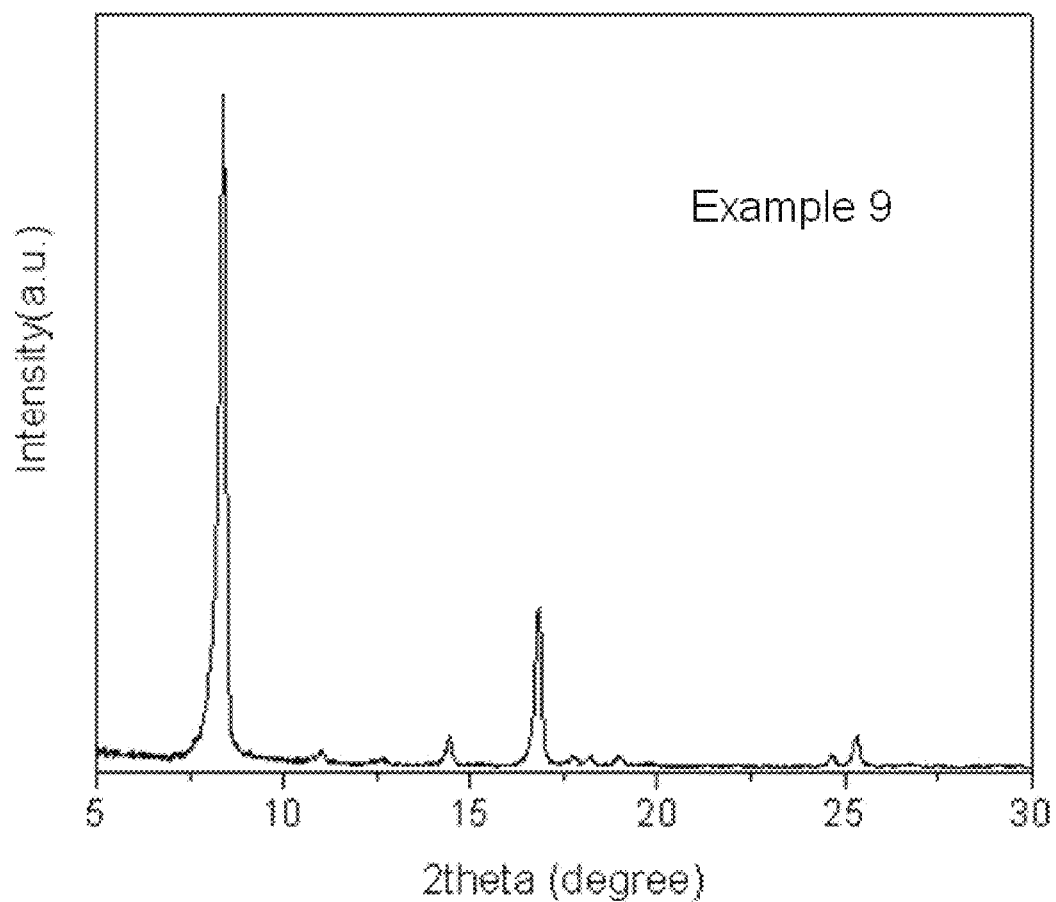
FIG. 6 is an X-ray diffraction pattern of the porous organic-inorganic hybrid (V-BDC).

In this Example, iron-series porous organic-inorganic hybrid is prepared by the same reflux method as example 1. In a 100 ml-glass flask containing 23.31 g of N,N-dimethylformamide, 13.36 g of ferrous chloride ($FeCl_3$—$H_2O$) is introduced and stirred at room temperature until dissolution of ferrous chloride, and then 11.2 g of 3,3',5,5'-azobenzenetetracarboxylic acid (AzoBTC) is added to give a reaction mixture havening a molar ratio of Fe:AzoBTC:DMF=1:0.6:12.9. The resulting reaction mixture is homogenized by stirred at room temperature and at a stirring speed of 100 rpm for 1 hours and heated to 70~80° C. to form an organogel. When the viscosity of the resulting organogel solution reaches 1500 cps, the stirring speed is lowered and maintained for 3 hours. The resulting reaction mixture is refluxed at a crystallization temperature of about 150° C. for 12 hours to complete the crystallization reaction. After completion of the reaction, the slurry solution containing the products is cooled to room temperature at a cooling rate of 5° C./min and filtered with a pressurized filter to obtain crystals. Thus obtained crystals are added to 300 ml of ethanol and stirred at 70° C. for 12 hours, and again filtered with a pressurized filter to remove unreacted acid and ligand. The above purification is repeated 2 more times to give a porous organic-inorganic hybrid (hereinafter, described in Fe-AzoBTC) with a high surface area, which has a Langmuir surface area of 1480 m$^2$/g. The X-ray diffraction pattern of thus obtained porous organic-inorganic hybrid is illustrated in FIG. 5, and it can be confirmed that X-ray diffraction pattern has the same diffraction pattern at the same positions with that of porous organic-inorganic hybrid MIL-127 reported in a reference document [WO2010/136677]. The organic-inorganic hybrid obtained in this Example has a very high space time yield of 130 kg/m$^3$.day.

Example 9

Preparation of a Porous Organic-Inorganic Hybrid

Example 6 is repeated with exception for using $VCl_3$ instead of iron chloride ($FeCl_3.6H_2O$) to obtain V-BDC. It is confirmed that thus prepared V-BDC has the values which are consistent to those reported in a reference document [*Chem. Chem. Phys.*, 10, 2979 (2008)] (see FIG. 5). It can be confirmed that the organic-inorganic hybrid obtained has a very high space time yield of 120 kg/m$^3$.day.

It can be confirmed that, by using the synthetic method according to the present invention, it is possible to prepare in a stable manner an organic-inorganic hybrid having a high surface area and a space time yield of more than 20 120 kg/m$^3$.day.

Example 10

Preparation of a Porous Organic-Inorganic Hybrid ZrO-BPDC

In a 25 ml round-bottomed glass flask equipped with a glass cooling condenser, 291 mg (1.2 mmol) of biphenyl-4,4'-dicarboxylic acid (4,4'-BPDC) and 5 ml (4.74 g, 64.9 mmol) of N,N-dimethylformamide are introduced and dissolved under stirring at room temperature, and then 186 mg (0.8 mmol) of $ZrCl_4$ and 0.13 ml (57 mg, 1.56 mmol) of aqueous HCl (37%, 12M) are added.

The resulting reaction mixture is heated to 70~80° C., and when the gelation is occurred, the stirring speed is lowered and maintained for 1 hour. Finally, the resulting reaction mixture is again raised to 150° C. and refluxed for 6 hours to perform the crystallization. After the reaction is completed, the cooling speed is adjusted to 5° C./min or more. The solid precipitation is filtered, washed successively with DMF and acetone, and then dried in an air to obtain crystals. It can be confirmed that the crystals thus obtained by the above method is a porous organic-inorganic hybrid having a high surface area, since the BET surface area is 671 m$^2$/g, measured by the physical adsorption of nitrogen at a temperature of −196° C.

Figure 7A:
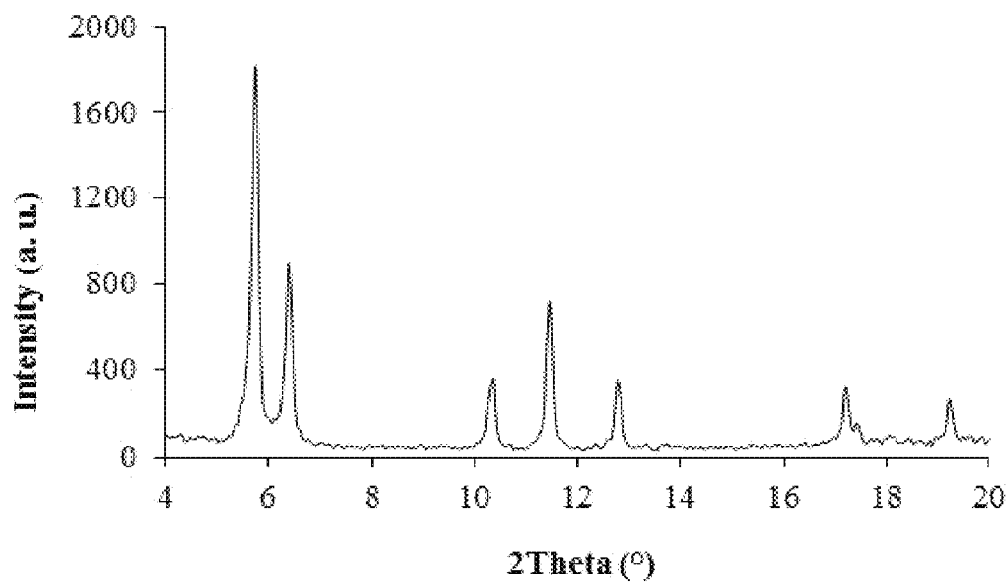
FIG. 7a is an X-ray diffraction pattern of the porous organic-inorganic hybrid (ZrO-BPDC) of Example 10.

The X-ray diffraction pattern of the porous organic-inorganic hybrid obtained in this Example is illustrated in FIG. 7a. It is confirmed that the porous organic-inorganic hybrid obtained in this Example has a chemical formula of ZrO [$(CO_2)_2(C_{12}H_8)$].n(Solvent) (wherein, n represents a rational number of 0~20 and a mol number of solvent molecules) (corresponding to Formula 3a), a space group of I2/a in the structure, and unit cell parameters of a=31.22, b=15.51 and c=7.82 wherein a, b and c mean each axe of the 3-dimensional space group.

Figure 7B:
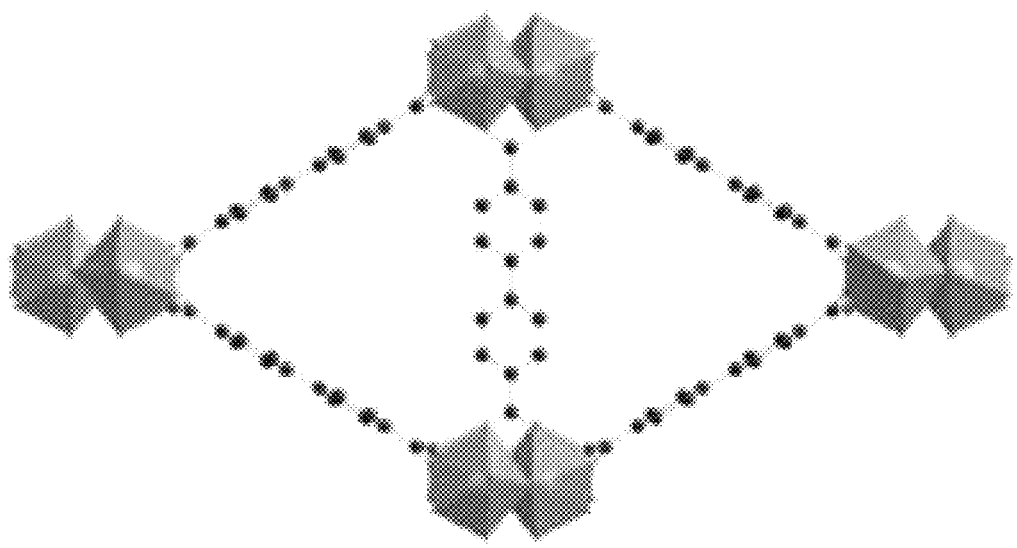
FIG. 7b is a crystal structure of c-axial direction of porous organic-inorganic hybrid (ZrO-BPDC) of Example 10.

The porous organic-inorganic hybrid ZrO-BPDC has a structural feature wherein channels formed by zirconium and 4,4'-BPDC have a triangular shape and are arranged to the c-axial direction. FIG. 7b shows a crystal structure of ZrO-BPDC obtained in this Example 10 when seen in the c-axial direction.

Example 11

Preparation of a Porous Organic-Inorganic Hybrid ZrO-AzoBDC

In a 25 ml round-bottomed glass flask equipped with a glass cooling condenser, 408 mg (1.2 mmol) of 3,3-dichloro-azobenzenedicarboxylic acid (4,4'-AzoBDC) and 5 ml (4.74 g, 64.9 mmol) of N,N-dimethylformamide are introduced and dissolved under stirring at room temperature, and then 186 mg (0.8 mmol) of $ZrCl_4$ and 0.13 ml (57 mg, 1.56 mmol) of aqueous HCl (37%, 12M) are added.

The resulting reaction mixture is heated to 70~80° C., and when the gelation is occurred, the stirring speed is lowered and maintained for 1 hour. Finally, the resulting reaction mixture is again raised to 150° C. and refluxed for 6 hours to perform the crystallization. After the reaction is completed, the cooling speed is adjusted to 5° C./min or more. The solid precipitation is filtered, washed successively with DMF and acetone, and then dried in an air to obtain crystals. It can be confirmed that the crystals thus obtained by the above method is a porous organic-inorganic hybrid having a high surface area, since the BET surface area is 418 m$^2$/g, measured by the physical adsorption of nitrogen at a temperature of −196° C.

Figure 8A:
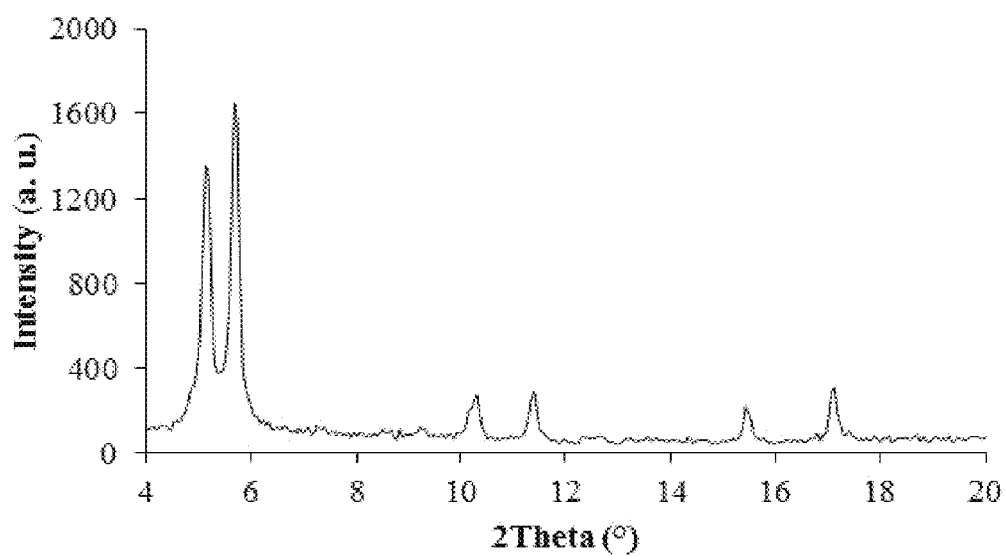
FIG. 8a is an X-ray diffraction pattern of porous organic-inorganic hybrid (ZrO-AzoBDC) of Example 11.

FIG. 8a illustrates the X-ray diffraction pattern of the porous organic-inorganic hybrid obtained in this Example. It is confirmed that the porous organic-inorganic hybrid obtained in this Example has a chemical formula of ZrO[(CO$_2$)$_2$(C$_{12}$H$_6$Cl$_2$N$_2$)].n(Solvent) (wherein, n represents a rational number of 0~20 and a mol number of solvent molecules) (corresponding to Formula 3b), a space group of Cc in the structure, and unit cell parameters of a=34.76, b=17.42 and c=7.45 wherein a, b and c mean each axe of the 3-dimensional space group.

Figure 8B:
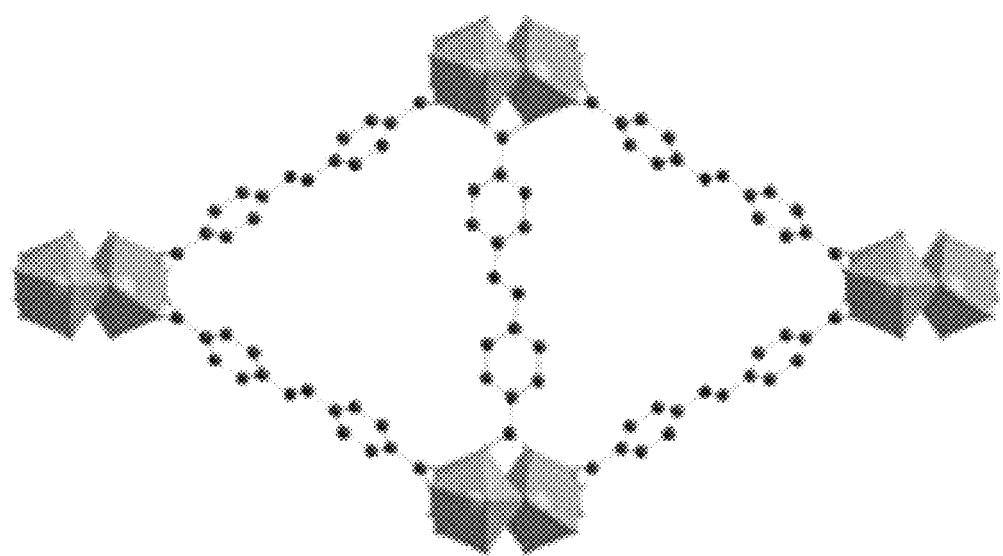
FIG. 8b is a crystal structure of c-axial direction of porous organic-inorganic hybrid (ZrO-AzoBDC) of Example 11.

The porous organic-inorganic hybrid ZrO-AzoBDC has a structural feature wherein channels formed by zirconium and dicarboxylic acid ligand have a triangular shape and are arranged to the c-axial direction. FIG. 8b shows a crystal structure of ZrO-AzoBDC obtained in this Example 11 when seen in the c-axial direction.

Example 12-16

Preparation of a Porous Organic-Inorganic Hybrid Using Water as Solvent

Example 12

In a Teflon reactor, 108 mg (0.6 mmol) of 2-aminoterephthalic acid (NH$_2$—H$_2$BDC), 70 mg (0.3 mmol) of ZrCl$_4$, 0.5 ml of H$_2$O and 0.5 ml of aqueous HCl solution (37%) are introduced. The resulting reaction mixture is heated to 80° C., and when the gelation is occurred, the stirring speed is lowered and maintained for 1 hour. Thereafter, the resulting reaction mixture is again raised to 100° C. and refluxed for 72 hours to perform the crystallization. After the reaction is completed, the reaction mixture is cooled and filtered to obtain the porous organic-inorganic hybrid Zr-BDC_NH$_2$ in powder form. Said Zr-BDC_NH$_2$ powder has a BET surface area of 1010 m$^2$/g at the dried state.

Thus obtained Zr-BDC_NH$_2$ powder has, when hydrated, has the following Formula 2a:

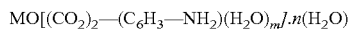

MO[(CO$_2$)$_2$—(C$_6$H$_3$—NH$_2$)(H$_2$O)$_m$].n(H$_2$O)

(wherein, M represents Zr, m represents a rational number of 0~20, and n represents a rational number of 0~20). Since said materials have functional groups directly coordinated to zirconium ion cluster as well as hydrophilic NH$_2$ functional groups, it has a feature that water molecules form a relatively strong hydrogen bond with the hydrophilic functional groups in the crystals prepared in an aqueous solution.

Figure 9:
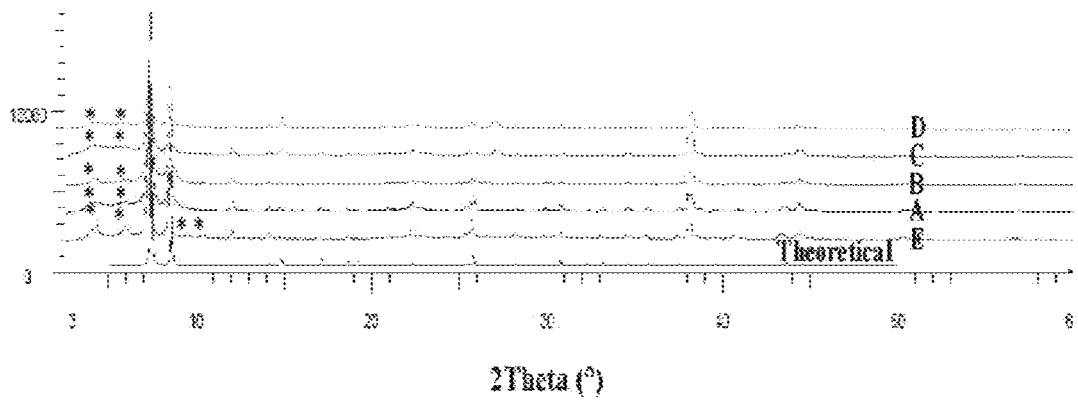
FIG. 9 is an X-ray diffraction pattern of porous organic-inorganic hybrid (Zr-BDC-$NH_2$) of Example 12.

FIG. 9 illustrates the X-ray diffraction pattern of the porous organic-inorganic hybrid synthesized in an aqueous solution of this Example.

Figure 10:
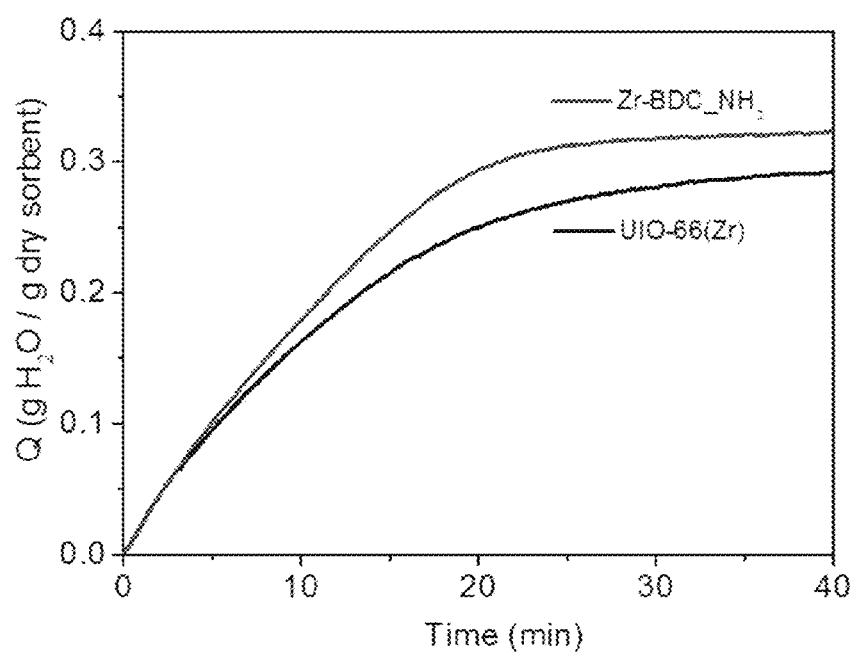
FIG. 10 is a comparing graph of water adsorption speed—adsorption amount of Example 12.

Since Zr-BDC_NH$_2$ contains a basic hydrophilic functional group to form a relatively strong hydrogen bond with water molecules, Zr-BDC_NH$_2$ is improved in hydrophilicity when compared with material without NH$_2$ functional group. For example, as can be seen in FIG. 10, dried Zr-BDC_NH$_2$ materials have a feature that the adsorption amount of water is improved at least 11% more than that of UiO-66(Zr), when the water adsorption rate and adsorption amount are measured at the condition of the temperature of 30° C. and the relative humidity of 70%.

Example 13

In a 1.2 ml-Teflon reactor, 63 mg (0.3 mmol) of 3-nitroterephthalic acid (NO$_2$—H$_2$BDC), 70 mg (0.3 mmol) of ZrCl$_4$, 0.5 ml of H$_2$O and 0.5 ml of aqueous HCl solution (37%) are introduced. The resulting reaction mixture is heated to 80° C., and when the gelation is occurred, the stirring speed is lowered and maintained for 1 hour. Thereafter, the resulting reaction mixture is again raised to 100° C. and refluxed for 72 hours to perform the crystallization. The reaction mixture is cooled, filtered, washed with water and acetone and dried to obtain the porous organic-inorganic hybrid Zr-BDC_NO$_2$ in powder form. Said Zr-BDC_NO$_2$ powder has a BET surface area of 865 m$^2$/g at the dried state.

Figure 11:
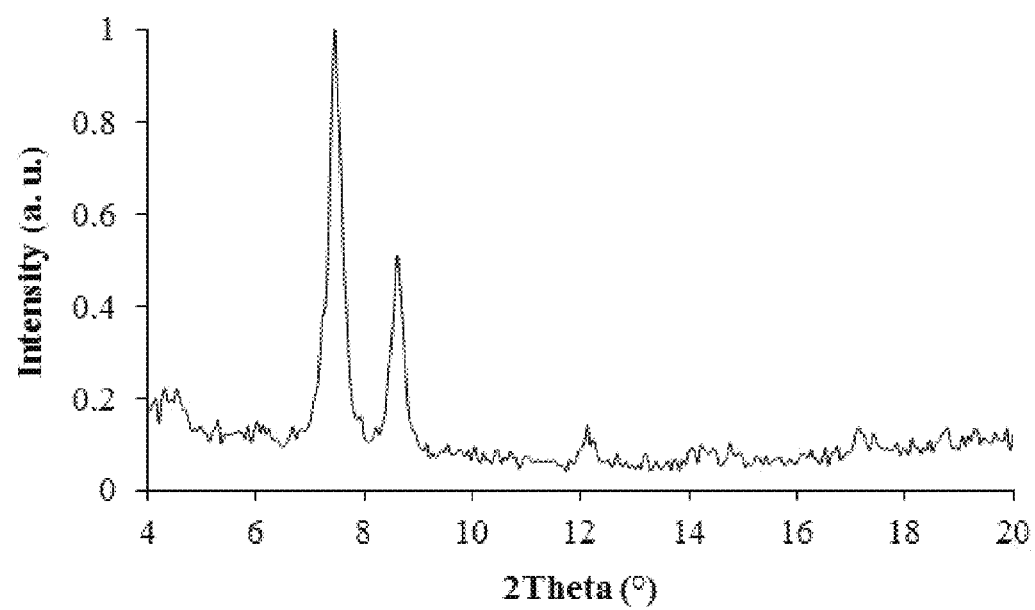
FIG. 11 is an X-ray diffraction pattern of porous organic-inorganic hybrid (Zr-BDC-$NO_2$) of Example 13.

FIG. 11 illustrates the X-ray diffraction pattern of the porous organic-inorganic hybrid synthesized in an aqueous solution of this Example.

Thus obtained powder (Zr-BDC_NO$_2$) has, when hydrated, has the following Formula 2b:

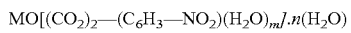

MO[(CO$_2$)$_2$—(C$_6$H$_3$—NO$_2$)(H$_2$O)$_m$].n(H$_2$O)

(wherein, M represents Zr, m represents a rational number of 0~20, and n represents a rational number of 0~20). Since said materials have polar functional groups to form a relatively strong hydrogen bond with water molecules, the hydrophilicity is improved when compared with materials without NO$_2$ functional groups.

Example 14

Example 12 is repeated except for using 108 mg (0.4 mmol) of 1,2,4,5-benzene-tetracarboxylic acid (H$_2$BDC-(COOH)$_2$) and 1 ml of H$_2$O to prepare a reaction mixture.

The porous organic-inorganic hybrid Zr-BDC_2 CO$_2$H obtained in this Example has a BET surface area of 680 m$^2$/g, measured by the physical adsorption of nitrogen at a temperature of −196° C.

Thus obtained powder (Zr-BDC_2CO$_2$H) has, when hydrated, has the following Formula 2d:

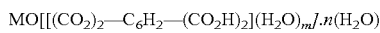

MO[[(CO$_2$)$_2$—C$_6$H$_2$—(CO$_2$H)$_2$](H$_2$O)$_m$].n(H$_2$O)

(wherein, M represents Zr, m represents a rational number of 0~20, and n represents a rational number of 0~20). Since said materials have carboxylate functional groups directly coordinated to zirconium ion cluster as well as acidic hydrophilic CO$_2$H functional groups, water molecules can form a relatively strong hydrogen bond with the hydrophilic functional groups in the crystals prepared in an aqueous solution to improve the water adsorption characterization. The dried Zr-BDC_2CO$_2$H materials have a feature that the adsorption amount of water is improved at least about 10% more than that of UiO-66(Zr), when the water adsorption rate and adsorption amount are measured at the condition of the temperature of 30° C. and the relative humidity of 70%.

Example 15

Example 12 is repeated except for using 85 mg (0.4 mmol) of 1,3,5-benzene-tricarboxylic acid (H$_2$BDC-CO$_2$H) and 1 ml of H$_2$O to prepare a reaction mixture and performing the gelation and crystallizing at the temperature of 100~150° C.

The porous organic-inorganic hybrid Zr-BDC_CO$_2$H obtained in this Example has a BET surface area of 690 m$^2$/g, measured at its dried state by the physical adsorption of nitrogen at a temperature of −196° C.

Thus obtained powder (Zr-BDC_CO₂H) has, when hydrated, has the following Formula 2c:

$$MO[[(CO_2)_2-C_6H_3-CO_2H](H_2O)_m].n(H_2O)$$

(wherein, M represents Zr, m represents a rational number of 0~20, and n represents a rational number of 0~20). Since said materials have functional groups directly coordinated to zirconium ion cluster as well as acidic hydrophilic CO₂H functional groups, water molecules can foiui a relatively strong hydrogen bond with the hydrophilic functional groups in the crystals prepared in an aqueous solution to improve the water adsorption characterization. The dried Zr-BDC_CO₂H materials have a feature that the adsorption amount of water is improved at least about 9% more than that of UiO-66(Zr), when the water adsorption rate and adsorption amount are measured at the condition of the temperature of 30° C. and the relative humidity of 70%.

Example 16

In a 100 ml-Teflon reactor, 4.56 g (0.017 mol) of sulfated terephthalic acid (H₂BDC-SO₃H), 2.332 g (0.001 mol) of ZrCl₄, 18 g (1.00 mol) of water are introduced. The resulting reaction mixture is stirred for about 1 hour and then heated to 90° C. for gelation, and when the gelation is occurred, the stirring speed is lowered and maintained for 1 hour. Thereafter, the resulting reaction mixture is heated at 150° C. for 12 hours. The reaction mixture is cooled, filtered and washed with water and ethanol to obtain the porous organic-inorganic hybrid in powder form.

The porous organic-inorganic hybrid Zr-BDC_SO₃H obtained in this Example has a BET surface area of 810 m²/g, measured at its dried state by the physical adsorption of nitrogen at a temperature of −196° C.

Thus obtained powder (Zr-BDC_SO₃H) has, when hydrated, has the following Formula 2e:

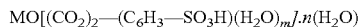

$$MO[(CO_2)_2-(C_6H_3-SO_3H)(H_2O)_m].n(H_2O)$$

(wherein, M represents Zr, m represents a rational number of 0~20, and n represents a rational number of 0~20). Since said materials have functional groups directly coordinated to zirconium ion cluster as well as acidic hydrophilic SO₃H functional groups, water molecules can form a relatively strong hydrogen bond with the hydrophilic functional groups in the crystals prepared in an aqueous solution to improve the water adsorption characterization. It can be observed that the dried Zr-BDC_SO₃H materials have a feature that the adsorption amount of water is improved at least 12% more than that of UiO-66(Zr), when the water adsorption rate and adsorption amount are measured at the condition of the temperature of 30° C. and the relative humidity of 70%.

Example 17-18

Mass Production of a Porous Organic-Inorganic Hybrid Using Water as Solvent

Example 17

In a 10 L-reactor, 412 g of 1,2,4,5-benzene-tetracarboxylic acid (H₂BDC-(COOH)₂), 450 g of ZrOCl₂, 1 L of H₂O and 1 L of aqueous HCl solution (37%) are introduced. The resulting reaction mixture is heated to 80° C., and when the gelation is occurred, the stirring speed is lowered and maintained for 1 hour. Thereafter, the resulting reaction mixture is raised to 100° C. and heated for 72 hours to perform the crystallization. After the reaction is completed, the reaction mixture is cooled and filtered to obtain the porous organic-inorganic hybrid Zr-BDC__2CO₂H in powder form. It can be confirmed that X-ray diffraction pattern of Zr-BDC__2CO₂H powder has the same diffraction pattern at the same positions with that of powder obtained in Example 14. The organic-inorganic hybrid obtained in this Example has a space time yield of 126 kg/m³.day.

Example 18

Example 16 is repeated except for using 340 g of 1,3,5-benzene-tricarboxylic acid (H₂BDC-CO₂H) in a 10 L-reactor. It can be confirmed that X-ray diffraction pattern of thus obtained Zr-BDC_CO₂H powder has the same diffraction pattern at the same positions with that of powder obtained in Example 15. The organic-inorganic hybrid obtained in this Example has a space time yield of 144 kg/m³.day.

INDUSTRIAL APPLICABILITY

The present invention provide a commercial preparation of a porous organic-inorganic hybrid in a high space-time yield in mild conditions such as in an aqueous solvent and at the atmospheric pressure or a slightly pressurized pressure, which can be used as absorbent materials for the storage, separation and the chemical reaction of gas, liquid and solid materials.

What is claimed is:

1. A method for the preparation of a porous organic-inorganic hybrid material having the following Formula 1:

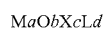

$$M_aO_bX_cL_d \qquad \text{[Formula 1]}$$

(wherein M represents a metal ion or an oxygen-bonded metal ion cluster, O represents an oxygen atom, X represents an anionic ligand, L represents an organic ligand, a represents a rational number of 1 to 12, b represents a rational number of 0 to 6, b represents a rational number of 0 to 18, and d represents a rational number of 1 to 120), characterized in that it comprises:
1) a step for obtaining a reaction mixture comprising a metal precursor comprising a metal ion or an oxygen-bonded metal ion cluster, a compound which can act as organic ligand, a water-soluble additive and water or water-containing organic solvent;
2) a step for heating said reaction mixture to a gelling temperature of 30~150° C. to give a organogel-containing solution having a viscosity of 2~50,000 (cps), which is then aged under stirring at the gelling temperature;
3) a step for further heating the resulted organogel-containing solution at a temperature between a temperature higher than said gelling temperature and 250° C. to crystallize the porous organic-inorganic hybrid.

2. The method according to claim 1, wherein said metal is at least one selected from a group consisting of Al, Cr, Fe, Hf, Mn, Ti, V, Zr, Ca and Mg.

3. The method according to claim 1, wherein said metal is at least one selected from a group consisting of Al, Cr, Fe, Hf, Mn and V.

4. The method according to claim 1, wherein said metal is at least one selected from a group consisting of Ti and Zr.

5. The method according to claim 1, wherein said metal ion or oxygen-bonded metal ion cluster is at least one compound selected from a group consisting of metal halide salt, metal oxyhalide salt, metal sulfate salt, metal oxysulfate salt, metal nitrate salt, metal acetate salt, metal carbonyl, metal alkoxide and hydrates thereof.

6. The method according to claim 1, wherein said reaction mixture of step 1) further comprises a compound which can act as an anionic ligand selected from a group consisting of at least one inorganic or organic compound containing $OH^-$, $F^-$, $Cl^-$, $Br^-$, $NO_3^-$, $BF_4^-$, $PF_6^-$, $I^-$, $SO_4^{2-}$, $HCO_3^-$ or $R_nCOO^-$ ($R_n$ represents a $C_1$-$C_6$ alkyl group).

7. The method according to claim 1, wherein said compound which can act as an organic ligand is at least one compound selected from a group consisting of benzenedicarboxylic acid, naphthalenedicarboxylic acid, biphenyldicarboxylic acid, azobenzenedicarboxylic acid, azobenzene tetracarboxylic acid, 1,3,5-tris(4-carboxyphenyl)benzene, benzenetricarboxylic acid, benzenetetracarboxylic acid, naphthalenetricarboxylic acid, fumaric acid, muconic acid, hexanedioic acid, heptandioic acid, and cyclohexyldicarboxylic acid.

8. The method according to claim 7, wherein said compound which can act as an organic ligand further possesses, in addition to the carboxylic acid substituents, at least one substituent selected from a group consisting of amino ($NH_2$), nitro ($NO_3$), hydroxy (OH), halide (X), sulfonic acid group ($SO_3H$).

9. The method according to claim 1, wherein said water-soluble additive is at least one acid selected from a group consisting of hydrochloric acid, nitric acid, sulfuric acid, phosphoric acid, acetic acid, boric acid and perchloric acid 10. The method according to claim 1, wherein said water-soluble additive is at least one salt or base or mixture thereof selected from a group consisting NaX (X=F—, Cl—, Br—, I—), $NaHCO_3$, $Na_2CO_3$, NaOH and $NH_4OH$.

11. The method according to claim 1, wherein said water-soluble additive is employed in a ratio of 0.01~10 mol per 1 mol of the metal ion.

12. The method according to claim 1, wherein said solvent is employed in a ratio of 1~30 mol per 1 mol of the metal ion.

13. The method according to claim 1, wherein the space-time yield of said porous organic-inorganic hybrid is 20 kg/day-m³ or more.

14. The method according to claim 1, wherein the solvent is water and the gelling agent is 80° C.~100° C.

15. The method according to claim 1, wherein said crystallization reaction in step 3) is carried out at a temperature between the gelling temperature and a temperature 10° C. higher than the gelling temperature.

16. The method according to claim 1, wherein said step 2) and 3) is carried out at the atmospheric pressure.

17. A porous organic-inorganic hybrid material comprising one or more metal ion cluster in which at least one IV metal ion is bonded with and one or more organic ligand having carboxylate functional group(s) which coordinately bond(s) to the metal ion cluster,
wherein said organic ligand further contains, in addition to the carboxylate functional group(s), one or more hydrophilic functional group as substituent, and said hydrophilic functional group forms hydrogen bond with water molecules in the crystal,
wherein said porous organic-inorganic hybrid material is represented by the following formula 2:

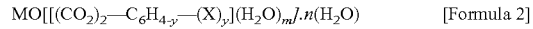  [Formula 2]

(wherein M represents Ti or Zr, O represents oxygen atom linked to a metal ion cluster, X represents a hydrophilic functional group which is substituted on the benzene ring and selected from —$NH_2$, —$NO_2$, —$CO_2H$ or $SO_3H$, y represent an integer of 1 to 4, m represents a rational number of 1 to 20, and n represents a rational number of 0 to 20).

18. The porous organic-inorganic hybrid material according to claim 17, comprising at least one hydrophilic basic functional group and represented by the following Formula 2a or 2b:

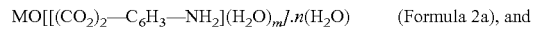  (Formula 2a), and

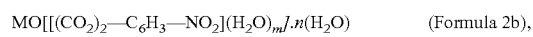  (Formula 2b), (wherein M represents Ti or Zr, m represents a rational number of 1 to 20, n represents a rational number of 0 to 20).

19. The porous organic-inorganic hybrid material according to claim 17, comprising at least one hydrophilic acidic functional group and represented by the following Formula 2c, 2d or 22:

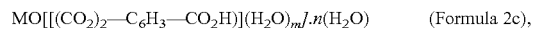  (Formula 2c),

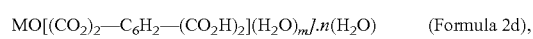  (Formula 2d), and

  (Formula 2e)

(wherein M represents Ti or Zr, m represents a rational number of 1 to 20, n represents a rational number of 0 to 20).

20. A porous organic-inorganic hybrid material consisting of one or more metal ion cluster in which at least one IV metal ion is bonded with and one or more organic ligand having carboxylate functional group(s) which coordinately bond(s) to the metal ion cluster,
wherein said organic ligand is selected from biphenyl-4,4'-dicarboxylic acid (4,4'-BPDC) or 3,3-dichloro-4,4'-azobenzenedicarboxylic acid (4,4'-AzoBDC)), and
wherein said porous organic-inorganic hybrid material has a space group of I2/a and is represented by the following Formula 3a or 3b:

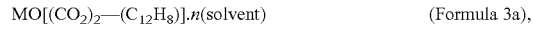  (Formula 3a),

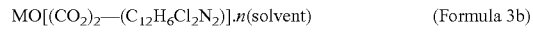  (Formula 3b)

(wherein M represents Ti or Zr, and n represents a rational number of 0 to 20).

* * * * *